US012222549B2

(12) United States Patent
Shelton (10) Patent No.: US 12,222,549 B2
(45) Date of Patent: Feb. 11, 2025

(54) ENDOSCOPE INCLUDING FIBER DELIVERY OF ILLUMINATION LIGHT

(71) Applicant: GYRUS ACMI, INC. D/B/A OLYMPUS SURGICAL TECHNOLOGIES AMERICA, Westborough, MA (US)

(72) Inventor: Kurt G. Shelton, Bedford, MA (US)

(73) Assignee: Gyrus ACMI, Inc., Westborough, MA (US)

(*) Notice: Subject to any disclaimer, the term of this patent is extended or adjusted under 35 U.S.C. 154(b) by 312 days.

(21) Appl. No.: 17/934,636

(22) Filed: Sep. 23, 2022

(65) Prior Publication Data

US 2023/0125384 A1 Apr. 27, 2023

Related U.S. Application Data

(60) Provisional application No. 63/362,930, filed on Apr. 13, 2022, provisional application No. 63/262,853, filed on Oct. 21, 2021.

(51) Int. Cl.
*G02B 6/26* (2006.01)
*A61B 1/00* (2006.01)
(Continued)

(52) U.S. Cl.
CPC .......... *G02B 6/262* (2013.01); *A61B 1/00096* (2013.01); *A61B 1/0017* (2013.01);
(Continued)

(58) Field of Classification Search
CPC ................ G02B 6/262; G02B 6/02057; G02B 6/02076; G02B 6/241; G02B 23/2469;
(Continued)

(56) References Cited

U.S. PATENT DOCUMENTS

2014/0180056 A1* 6/2014 Hoseit .................... A61N 5/062
600/407
2017/0035281 A1* 2/2017 Takeuchi ............... H04N 23/56
(Continued)

FOREIGN PATENT DOCUMENTS

CN 115998228 4/2023

*Primary Examiner* — Michelle R Connelly
(74) *Attorney, Agent, or Firm* — Schwegman Lundberg & Woessner, P.A.

(57) ABSTRACT

An endoscope can include an elongated endoscope body. An optical fiber can extend along the endoscope body. The optical fiber can direct therapeutic light and illumination light longitudinally along the optical fiber to a distal portion of the endoscope body. The therapeutic light and the illumination light can have different wavelengths. A wavelength-sensitive light separator, disposed at a distal portion of the optical fiber, can direct the illumination light to exit the optical fiber laterally through a lateral side of the optical fiber at the distal portion of the optical fiber and permit the therapeutic light to exit the optical fiber longitudinally through a distal end of the optical fiber. Examples of suitable wavelength-sensitive light separators can include one or more fiber Bragg gratings that can be obliquely angled, or a diffraction grating disposed on a lateral edge of a length of coreless fiber.

20 Claims, 5 Drawing Sheets (51) Int. Cl.
  *A61B 1/06*  (2006.01)
  *A61B 1/07*  (2006.01)
  *G01D 5/353*  (2006.01)
  *G02B 6/02*  (2006.01)
  *G02B 6/24*  (2006.01)
  *G02B 23/24*  (2006.01)
  *G02B 27/42*  (2006.01)

(52) U.S. Cl.
  CPC .............. *A61B 1/0623* (2013.01); *A61B 1/07* (2013.01); *G01D 5/35316* (2013.01); *G02B 6/02057* (2013.01); *G02B 6/02076* (2013.01); *G02B 6/241* (2013.01); *G02B 23/2469* (2013.01); *A61B 1/0638* (2013.01); *G02B 6/02138* (2013.01); *G02B 27/4244* (2013.01)

(58) Field of Classification Search
  CPC ............ G02B 6/02138; G02B 27/4244; G02B 23/2415; G02B 23/2423; G02B 23/243; G02B 23/2438; G02B 6/34; A61B 1/00096; A61B 1/0017; A61B 1/0623; A61B 1/07; A61B 1/0638; A61B 1/00165; A61B 1/00167; A61B 1/0661; A61B 1/0669; A61B 1/0676; A61B 1/0684; A61B 1/0692; A61B 5/0084; A61B 8/12; A61B 5/6851; A61B 5/6852; G01D 5/35316
  See application file for complete search history.

(56) References Cited

U.S. PATENT DOCUMENTS

| | | | |
|---|---|---|---|
| 2017/0160132 A1* | 6/2017 | Shishkov | ............... A61B 1/002 |
| 2019/0094458 A1* | 3/2019 | Ohara | .................. A61B 1/0653 |
| 2019/0254530 A1 | 8/2019 | Rourke et al. | |
| 2019/0374092 A1* | 12/2019 | Wu | .................... G02B 23/2469 |

* cited by examiner

ENDOSCOPE INCLUDING FIBER DELIVERY OF ILLUMINATION LIGHT

PRIORITY CLAIMS

This application claims the benefit of priority to U.S. Provisional Patent Application Ser. No. 63/262,853 filed Oct. 21, 2021, and U.S. Provisional Patent Application Ser. No. 63/362,930, filed Apr. 13, 2022; the contents of which are hereby incorporated by reference.

FIELD OF THE DISCLOSURE

The present disclosure relates generally to an endoscope.

BACKGROUND OF THE DISCLOSURE

Endoscopes are light-delivery devices that can illuminate a target and deliver images of the illuminated target. Endoscopes can be customized in size, shape, and function to examine particular organs in a patient, for a variety of medical procedures. For example, a nephroscope is an endoscope that is designed to illuminate and view a kidney stone or other object within a region of a kidney. Similarly, a cystoscope is an endoscope that can illuminate and view portions of a bladder. Other types of endoscopes, which can include laparoscopes, can be used to examine other organs.

There is ongoing effort to improve endoscopes.

SUMMARY

In an example, an endoscope can include: an elongated endoscope body; an optical fiber extending along the endoscope body, the optical fiber configured to direct therapeutic light and illumination light longitudinally along the optical fiber to a distal portion of the endoscope body, the therapeutic light and the illumination light having different wavelengths; and a wavelength-sensitive light separator disposed at a distal portion of the optical fiber, the wavelength-sensitive light separator configured to direct the illumination light to exit the optical fiber laterally through a lateral side of the optical fiber at the distal portion of the optical fiber and permit the therapeutic light to exit the optical fiber longitudinally through a distal end of the optical fiber.

In an example, a method for delivering light in an endoscope can include: directing therapeutic light and illumination light longitudinally along an optical fiber to a distal portion of an elongated endoscope body, the therapeutic light and the illumination light having different wavelengths; directing, with a wavelength-sensitive light separator, the illumination light to exit the optical fiber laterally through a lateral side of the optical fiber at the distal portion of the optical fiber; and permitting, with the wavelength-sensitive light separator, the therapeutic light to exit the optical fiber longitudinally through a distal end of the optical fiber.

In an example, an endoscope can include: an elongated endoscope body; an optical fiber extending along the endoscope body, the optical fiber configured to direct infrared therapeutic light and visible illumination light longitudinally along the optical fiber to a distal portion of the endoscope body; and an obliquely-angled fiber Bragg grating disposed along a length of the distal portion of the optical fiber, the obliquely-angled fiber Bragg grating configured to reflect at least some of the visible illumination light out of the optical fiber through a lateral side of the optical fiber and transmit the infrared therapeutic light through the obliquely-angled fiber Bragg grating to exit the optical fiber longitudinally through a distal end of the optical fiber.

BRIEF DESCRIPTION OF THE DRAWINGS

Corresponding reference characters indicate corresponding parts throughout the several views. Elements in the drawings are not necessarily drawn to scale. The configurations shown in the drawings are merely examples and should not be construed as limiting in any manner.

DETAILED DESCRIPTION

An endoscope can include an optical fiber that can direct therapeutic light and illumination light longitudinally along the optical fiber to a distal portion of the endoscope. The therapeutic light and the illumination light can have different wavelengths. For example, the illumination light wavelengths can fall within the visible light portion of the electromagnetic energy spectrum, while the therapeutic light wavelengths are not so limited. At a distal portion of the optical fiber, the optical fiber can direct the therapeutic light to exit the optical fiber longitudinally through a distal end of the optical fiber and direct the illumination light to exit the optical fiber circumferentially through a lateral side of the optical fiber at the distal portion of the optical fiber.

Figure 13:
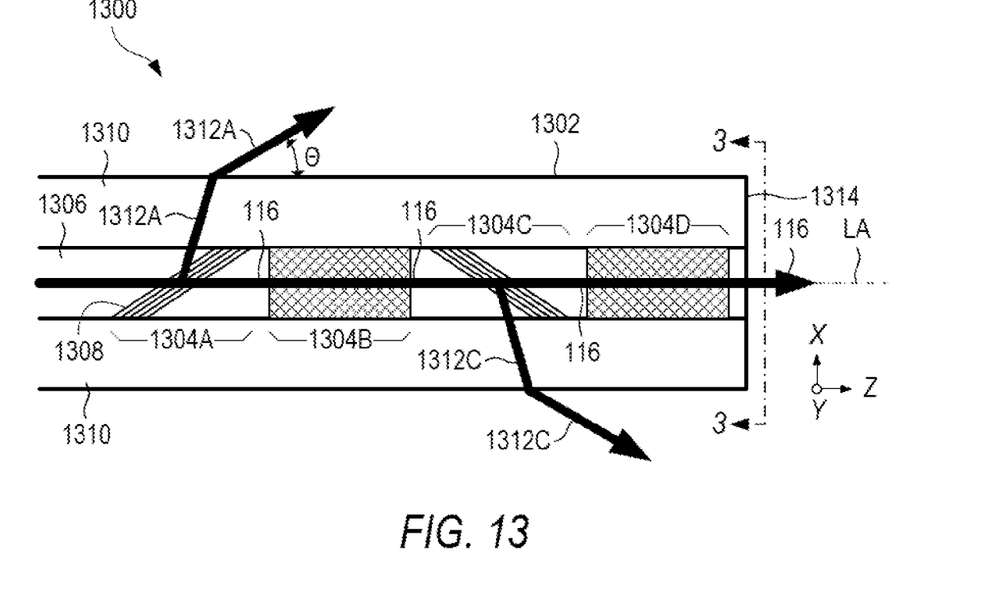
FIG. 13 a cross-sectional side view of an example of a distal portion of an optical fiber, suitable for use in the endoscope of FIG. 1.
Figure 14:
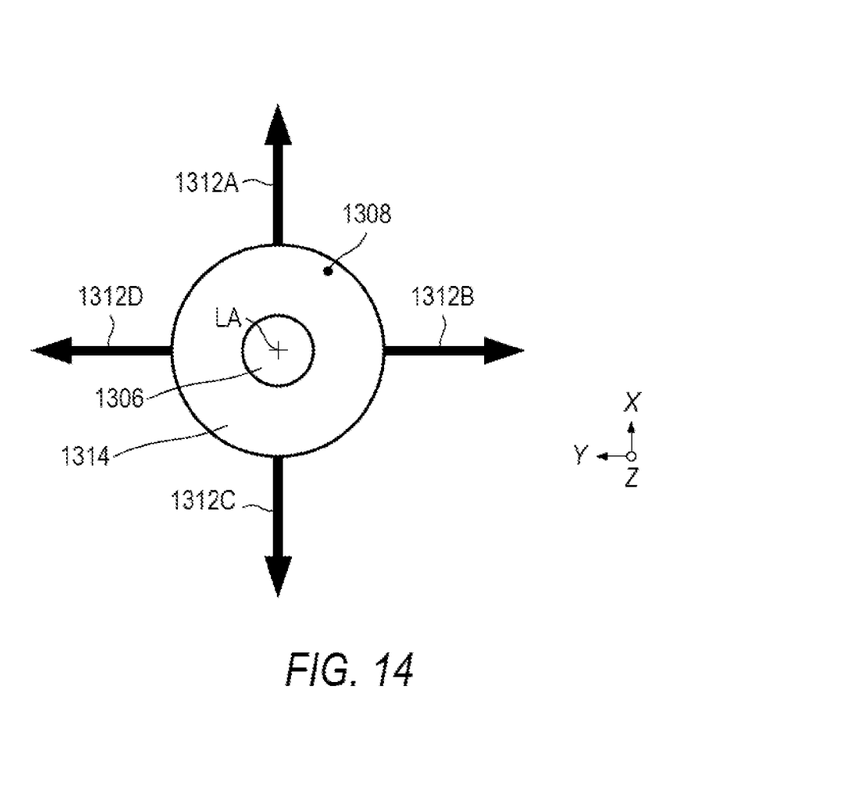
FIG. 14 shows an end-on view of a distal end of the optical fiber of FIG. 13.

In some examples, the therapeutic light and the illumination light can propagate, combined, along the optical fiber to the distal portion of the optical fiber. In these examples, a wavelength-sensitive light separator, such as a diffraction grating, can split the illumination light from the therapeutic light. FIGS. 2-7 show examples of optical fiber configurations in which the therapeutic light and the illumination light can propagate, combined, along the optical fiber. FIGS. 13 and 14 show another example of an optical fiber configuration in which the therapeutic light and the illumination light can propagate, combined, along the optical fiber.

In some examples, the optical fiber can include multiple cores that can keep the therapeutic light and the illumination light separate as the therapeutic light and the illumination light propagate along the optical fiber. In these examples, the optical fiber can allow light from only one of the cores to exit the optical fiber through the lateral side of the optical fiber, such as by thinning the optical fiber in the vicinity of one of the cores. FIGS. 8-11 show examples of optical fiber configurations in which the therapeutic light and the illumination light can propagate, separately, along separate cores in the optical fiber. In some examples, a fiber bundle can be used, which can propagate the therapeutic light and the illumination light in different fibers in the fiber bundle to the distal portion of the fiber bundle.

Compared with an endoscope that includes an illuminating light source, such as a light-emitting diode, at its distal tip, the endoscope described in detail below can lack the light-emitting diode and its associated circuitry. As a result, the endoscope described in detail below can have a decreased complexity (and, therefore, a lower cost) and can produce less heat at its distal end than the comparable endoscope that includes an illuminating light source at its distal tip.

Figure 1:
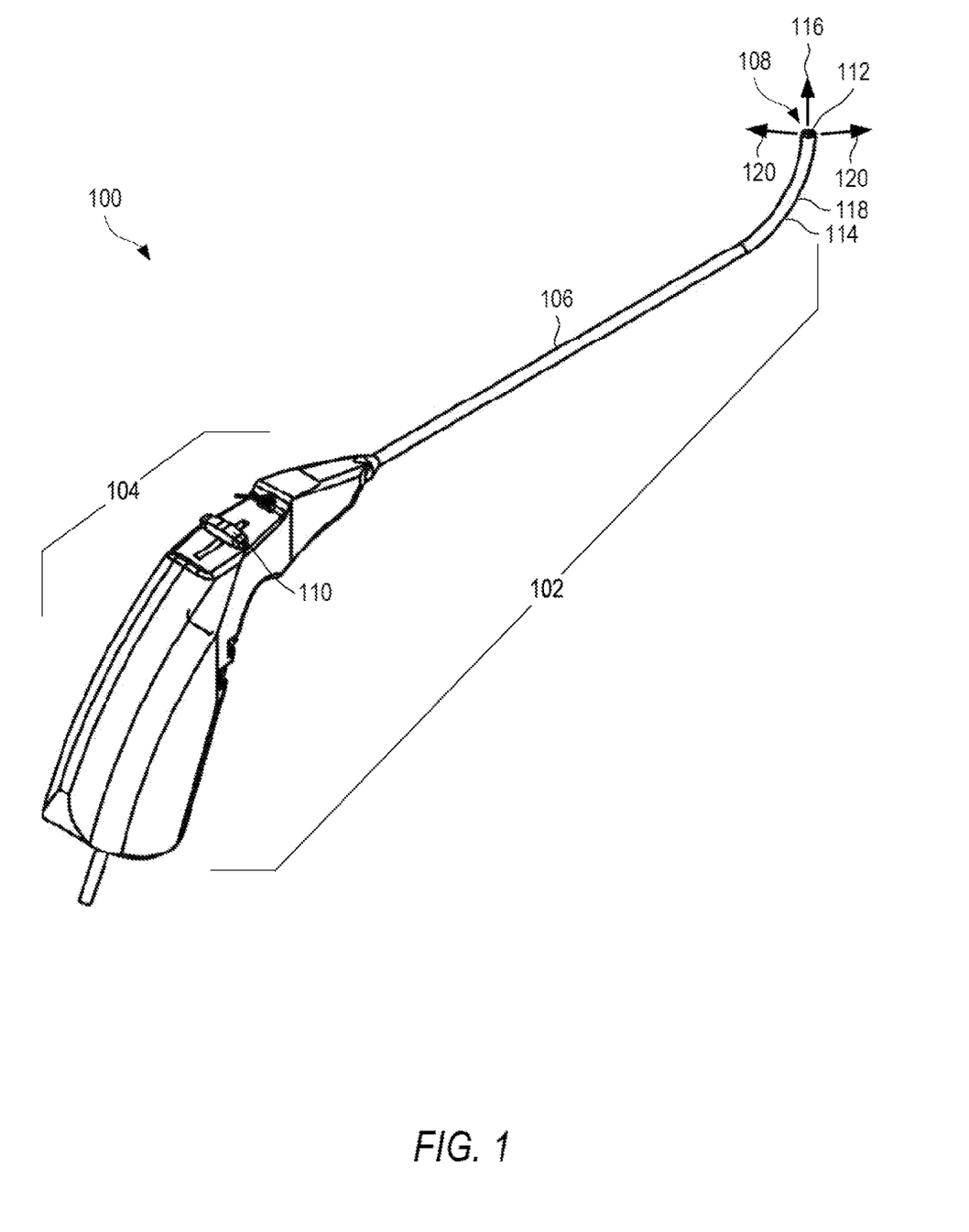
FIG. 1 shows a perspective view of an example of an endoscope.

FIG. 1 shows a perspective view of an example of an endoscope 100. The configuration of FIG. 1 is but one example of an endoscope; other configurations can also be used.

As used in this document, the term endoscope includes a class of devices that can illuminate an organ of a patient or a target within a patient's body, capture an image of the illuminated organ or target, and, optionally, deliver a treatment to the organ or target. Endoscopes that are shaped and sized for particular organs or procedures may be referred to by more specific names. For example, a cystoscope is shaped and sized to treat a patient's bladder, a nephroscope is shaped and sized to treat a patient's kidney, a bronchoscope is shaped and sized to treat a patient's bronchus, an arthroscope is shaped and sized to treat particular joints, a colonoscope is shaped and sized to treat a patient's colon, a laparoscope is shaped and sized to treat a patient's abdomen or pelvis, and so forth. Each of these specific names can refer to a particular type of endoscope. For simplicity, the endoscope 100 is described below as being configured to treat kidney stones; it will be understood that treating kidney stones is but one example of use of the endoscope 100, and that other uses are possible.

The endoscope 100 can include an elongated endoscope body 102 that is at least partially insertable into a body of a patient. The endoscope body 102 can include a grippable proximal portion 104. The endoscope body 102 can include an elongated portion 106 that extends from the grippable proximal portion 104. The elongated portion 106 can be rigid throughout or can have one or more portions that are flexible. The elongated portion 106 can extend to a distal endoscope body portion 108. The endoscope body 102 can include an articulation controller 110 on the grippable proximal portion 104 of the endoscope body 102. The articulation controller 110 can adjust a position of the distal endoscope body portion 108 to locate a target, such as a kidney stone, when the endoscope body 102 is inserted into a kidney of the patient. The endoscope body 102 can include a video camera 112 located at a distal end of the distal endoscope body portion 108. The endoscope body 102 can include electrical connections 114 for power and a data signal that represents the captured video image. The electrical connections 114 can extend from the grippable proximal portion 104, along the elongated portion 106, to the distal endoscope body portion 108. The video camera 112 can capture a video image of the target and/or illuminated tissue surrounding the target. During a procedure, the distal endoscope body portion 108 can illuminate the target, provide a video image of the illuminated target, ablate the target, and, optionally, remove all or a portion of the ablated target.

To ablate the target, the distal endoscope body portion 108 can deliver therapeutic light 116 onto the target or onto fluid proximate the target. The target, or the fluid proximate the target, can absorb all or a portion of the therapeutic light 116, and, in response, can vaporize. The vaporized fluid can mechanically shock the kidney stone. Repeated emission, absorption, and mechanically shocking the kidney stone in this manner can break the kidney stone into smaller pieces. A practitioner can remove the smaller kidney stone pieces through the endoscope body 102. The practitioner can use the illuminating and imaging features of the endoscope 100 to determine that all the kidney stone pieces have been extracted from the patient. The practitioner can then remove the endoscope body 102 from the body of the patient.

The endoscope 100 can include an optical fiber 118 that extends along the endoscope body 102. The optical fiber 118 can direct the therapeutic light 116 and illumination light 120 longitudinally along the optical fiber 118 to the distal endoscope body portion 108. A proximal end of the optical fiber 118 can removably couple to one or more light sources, such as a pulsed laser for the therapeutic light 116 and one or more light-emitting diodes for the illumination light 120. Therapeutic light 116 from the pulsed laser can propagate longitudinally along the optical fiber 118, from the proximal portion 104 to the distal endoscope body portion 108 of the endoscope body 102 and can emerge from a distal end of the optical fiber 118 to perform the treatment. By using the optical fiber 118 to deliver the therapeutic light 116 (as opposed to including the therapeutic light source in the endoscope body 102), the endoscope 100 can be used with any suitable light source, and/or can switch from a first light source to a second light source during a procedure without removing the endoscope body 102 from the patient.

The therapeutic light 116 and the illumination light 120 can have different wavelengths.

The therapeutic light 116 can be absorbed by a target or by fluid surrounding a target. Because the therapeutic light 116 is intended to be absorbed by a fluid, such as water, the therapeutic light 116 can have a spectrum that includes one or more wavelengths at which water has a relatively high absorption. Water can have a relatively high absorption for particular wavelengths (e.g., peaks) or wavelength regions (e.g., relatively broad spectral regions) in the infrared portion of the electromagnetic spectrum. In some examples, the therapeutic light 116 can have a wavelength in the infrared portion of the electromagnetic spectrum. In some examples, the therapeutic light 116 can have a wavelength corresponding to an emission wavelength of a pulsed thulium laser. In some examples, the therapeutic light 116 can have a wavelength between 1810 nm and 2100 nm. In some examples, the therapeutic light 116 can have a wavelength of about 1940 nm. Other wavelengths or wavelength regions can also be used. In some examples, the therapeutic light 116 can be produced by an infrared laser, such as a pulsed thulium laser, and coupled into a proximal end of the optical fiber 118.

The illumination light 120 can illuminate an area or a volume proximate the distal end of the optical fiber 118. Because the illumination light 120 is intended to visibly illuminate a target or a portion of tissue, the illumination light 120 can have a spectrum that includes all or a portion of the visible portion of the electromagnetic spectrum. In some examples, the illumination light 120 can have at least one wavelength between 400 nm and 700 nm. In some examples, the illumination light 120 can include a continuum of wavelengths, at least a portion of the continuum of wavelengths being between 400 nm and 700 nm. In some examples, the illumination light 120 can be white light, having a spectrum that is perceived as white or nearly white when viewed by a human eye. In some examples, the illumination light 120 can be produced by a white-light light-emitting diode and coupled into a proximal end of the optical fiber 118.

Figure 2:
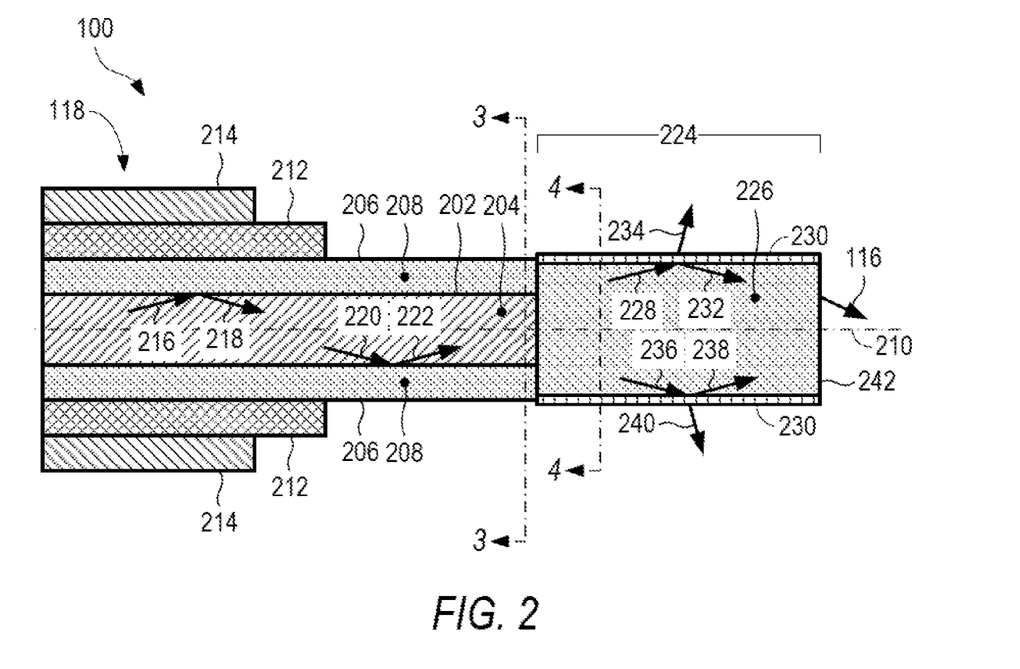
FIG. 2 shows a cross-sectional side view of an example of a distal portion of the optical fiber, for the endoscope of FIG. 1.

FIG. 2 shows a cross-sectional side view of an example of a distal portion of the optical fiber 118, for the endoscope 100 of FIG. 1.

The optical fiber 118 can include a core 202 that is elongated and extends along a length of the optical fiber 118. The core 202 can be formed from a core material 204 having a core refractive index. The core material 204 can be relatively transparent (e.g., having a relatively low absorption) over the range of wavelengths of the therapeutic light 116 and the illumination light 120.

The optical fiber 118 can include a cladding 206 that surrounds the core 202 along the length of the optical fiber 118. The cladding 206 can be formed from a cladding material 208 having a cladding refractive index that is less than the core refractive index. The cladding material 208 can be relatively transparent (e.g., having a relatively low absorption) over the range of wavelengths of the therapeutic light 116 and the illumination light 120.

For simplicity, the optical fiber 118 described herein is shown as being a step-index optical fiber 118, which includes a discrete (and smooth) boundary between the core 202 (having a core refractive index) and the cladding 206 (having a cladding refractive index less than the core refractive index). Alternatively, a graded-index optical fiber 118 can also be used, in which the refractive index can vary continuously as a function of distance away from a longitudinal axis 210 of the optical fiber 118. Either a step-index optical fiber 118 or a graded-index optical fiber 118 can be used in the endoscope 100.

In some examples, the optical fiber 118 can be a multimode optical fiber 118. In a multimode optical fiber 118, guided light remains mostly in the core 202 as it propagates and reflects from the cladding 206 via total internal reflection at the boundary between the core 202 and the cladding 206. The boundary between the core 202 and the cladding 206 can be relatively smooth, so that total internal reflection can be supported at each location on the boundary. For example, a guided light ray 216 in the core 202 can strike the cladding 206 and reflect via total internal reflection from the cladding 206 as a reflected guided light ray 218. Similarly, a guided light ray 220 in the core 202 can strike the cladding 206 and reflect via total internal reflection from the cladding 206 as a reflected guided light ray 222. In a multimode optical fiber 118, the core 202 can be relatively large compared to a wavelength of the guided light, such as being larger than the wavelength by a factor of 50, 100, 200, or greater than a factor of 200. Core diameters for certain multimode optical fibers 118 can include 50 microns 62.5 microns, 100 microns, and 200 microns, although other suitable values can also be used. Cladding diameters for certain multimode optical fibers 118 can include 80 microns and 125 microns, although other suitable values can also be used.

In some examples, the optical fiber 118 can be a single-mode optical fiber 118. In a single-mode optical fiber 118, the guided light can have a generally invariant mode shape as the light propagates along the single-mode optical fiber 118 (as opposed to individual light rays propagating by repeatedly reflecting from the boundary between the core 202 and the cladding 206). In a single-mode optical fiber 118, guided light can include significantly amounts of optical power in both the core 202 and the cladding 206. In a single-mode optical fiber 118, the core 202 can be slightly larger than the wavelength of the guided light, such as being larger than the wavelength by a factor of ten, five, or less than five. Core diameters for certain single-mode optical fibers 118 can be between 8 microns and 10 microns, although other suitable values can also be used. Cladding diameters for certain multimode optical fibers 118 can include 80 microns and 125 microns, although other suitable values can also be used.

The optical fiber 118 can include additional non-optical elements that are structural in nature, and may not transmit light (e.g., may be opaque). An inner jacket 212 can surround the cladding 206. An outer jacket 214 can surround the inner jacket 212. An outer jacket diameter 214 for a certain single-mode optical fiber 118 can include 900 microns, although other suitable values can also be used. The inner jacket 212 and the outer jacket diameter 214 can stop short of a distal portion of the optical fiber 118, so that an outer surface of the distal portion may be exposed and may not be covered by the inner jacket 212 and the outer jacket 214.

Figure 3:
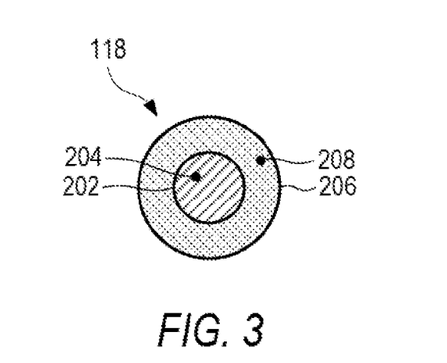
FIG. 3 shows an end-on cross-sectional view of the optical fiber of FIG. 2, the cross-section being taken orthogonal to the longitudinal axis of the optical fiber in a region that lacks the inner jacket and the outer jacket.

FIG. 3 shows an end-on cross-sectional view of the optical fiber 118 of FIG. 2, the cross-section being taken orthogonal to the longitudinal axis 210 of the optical fiber 118 in a region that lacks the inner jacket 212 and the outer jacket 214. The cross-sectional view shows the core 202, formed from a core material 204, surrounded by a cladding 206, formed from a cladding material 208. In some examples, both the core 202 and the cladding 206 can be rotationally symmetric about the longitudinal axis 210 of the optical fiber 118. In some examples, both the core 202 and the cladding 206 can have circularly symmetric cross-sections. Other symmetric and asymmetric configurations can also be used.

Returning to FIG. 2, the optical fiber 118 can include an optical fiber distal portion 224 that can have a different structure than the optical fiber 118 proximal to the optical fiber distal portion 224.

As a first example of the optical fiber distal portion 224 having a different structure than the optical fiber 118 proximal to the optical fiber distal portion 224, the optical fiber distal portion 224 can lack the core/cladding structure that guides the light in the optical fiber 118. In some examples, the optical fiber distal portion 224 can have a substantially uniform refractive index. For example, the optical fiber distal portion 224 can be formed as a length of core-free fiber (e.g., just cladding, without the core) that is spliced, fused, or otherwise attached to a distal end of the optical fiber 118. The optical fiber distal portion 224 can be formed from a material 226 that is the core material 204, the cladding material 208, or another suitable material having a refractive index relatively close to the core material refractive index or the cladding material refractive index (e.g., to within a value of 0.2, 0.1, 0.05, or another suitable value).

The therapeutic light 116 and the illumination light 120 can propagate as guided light longitudinally along the optical fiber 118. The optical fiber distal portion 224 can receive the guided light and propagate the guided light distally within the optical fiber distal portion 224 as unguided light. The unguided light can expand radially as it propagates distally within the optical fiber distal portion 224 to strike a lateral side, such as a circumferential exterior surface, of the optical fiber distal portion 224. For example, an unguided light ray 228 can strike a wavelength-sensitive light separator 230 (described in detail below), with some or all of the therapeutic light being reflected to form a reflected ray 232, and some or all of the illumination light being transmitted to form a transmitted ray 234. Similarly, an unguided light ray 236 can strike the wavelength-sensitive light separator 230, with some or all of the therapeutic light being reflected to form a reflected ray 238, and some or all of the illumination light being transmitted to form a transmitted ray 240. The transmitted rays 234 and 240 can form the illumination light 120 (FIG. 1). The reflected rays 232 and 238 can transmit through a distal end 242 of the optical fiber 118 to form the therapeutic light 116 (FIG. 1).

Figure 4:
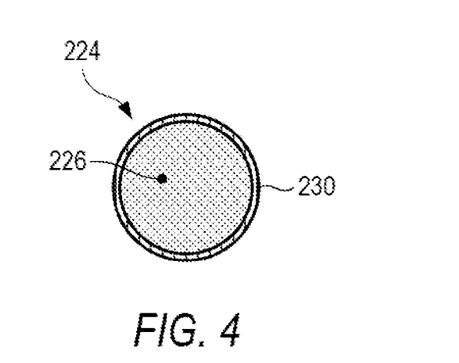
FIG. 4 shows an end-on cross-sectional view of the optical fiber distal portion of FIG. 2, the cross-section being taken orthogonal to the longitudinal axis of the optical fiber, for a first example of the optical fiber distal portion having a different structure than the optical fiber proximal to the optical fiber distal portion.

FIG. 4 shows an end-on cross-sectional view of the optical fiber distal portion 224 of FIG. 2, the cross-section being taken orthogonal to the longitudinal axis 210 of the optical fiber 118, for the first example of the optical fiber distal portion 224 having a different structure than the optical fiber 118 proximal to the optical fiber distal portion 224. The view of FIG. 4 shows material 226 lacking a core/cladding structure (such as having a uniform refractive index) and being at least partially surrounded by the wavelength-sensitive light separator 230 (described in detail below).

Other configurations are possible for the optical fiber distal portion 224. For clarity, these other configurations are shown in cross-section, similar to the view of FIG. 4. It will be understood that any or all of the optical fiber distal portion configurations described herein can be used with any or all of the fiber configurations described herein. For the discussion that follows, the optical fiber distal portion 224 is considered to be part of the optical fiber 118, such that a distal end 242 of the optical fiber 118 includes the optical fiber distal portion 224.

Figure 5:
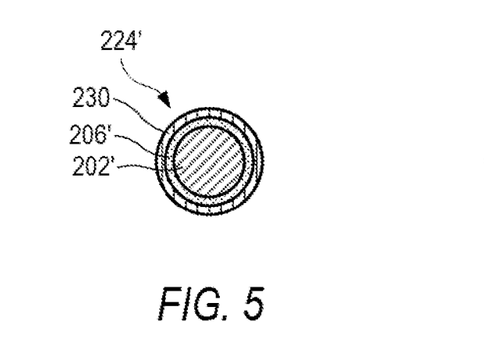
FIG. 5 shows an end-on cross-sectional view of an example of an optical fiber distal portion, the cross-section being taken orthogonal to the longitudinal axis of the optical fiber, for a second example of the optical fiber distal portion having a different structure than the optical fiber proximal to the optical fiber distal portion.

FIG. 5 shows an end-on cross-sectional view of an example of an optical fiber distal portion 224', the cross-section being taken orthogonal to the longitudinal axis 210 of the optical fiber 118, for a second example of the optical fiber distal portion 224' having a different structure than the optical fiber proximal to the optical fiber distal portion 224'.

In the second example of the optical fiber distal portion 224' having a different structure than the optical fiber proximal to the optical fiber distal portion 224', the cladding 206' can have a reduced thickness in the optical fiber distal portion 224'. Such a reduced cladding thickness can allow the therapeutic light and the illumination light to strike a circumferential exterior surface of the optical fiber distal portion 224', optionally retaining the same core 202' as used in the full length of the optical fiber. In some examples, the cladding 206' can have a first thickness proximate a midpoint between the optical fiber distal portion 224' of the optical fiber and a proximal portion of the optical fiber, and a second thickness at the optical fiber distal portion 224' of the optical fiber, where the second thickness can be less than the first thickness. The wavelength-sensitive light separator 230 (described in detail below) can at least partially surround the cladding 206'.

The optical fiber distal portion 224 of the optical fiber 118 can include a wavelength-sensitive light separator 230 (FIGS. 2, 4, and 5). The wavelength-sensitive light separator 230 can be disposed on a lateral surface or a lateral side of the optical fiber distal portion 224 (or 224') of the optical fiber 118. The wavelength-sensitive light separator 230 can direct the therapeutic light 116 to exit the optical fiber 118 longitudinally through a distal end of the optical fiber 118 (FIGS. 1 and 2). The wavelength-sensitive light separator 230 can direct the illumination light 120 to exit the optical fiber 118 circumferentially through the lateral side of the optical fiber 118 at the optical fiber distal portion 224 of the optical fiber 118 (FIGS. 1 and 2).

Figure 6:
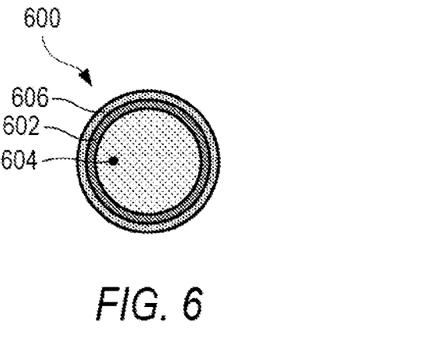
FIG. 6 shows an end-on cross-sectional view of an example of an optical fiber distal portion.

FIG. 6 shows an end-on cross-sectional view of an example of an optical fiber distal portion 600. In some examples, the wavelength-sensitive light separator can include a dichroic thin-film coating 602 disposed on the lateral side of the optical fiber at the optical fiber distal portion 600. The dichroic thin-film coating 602 can reflect at least some of the therapeutic light and transmit at least some of the illumination light. In some examples, the optical fiber distal portion 600 can be formed from a material 604 having a refractive index that is invariant over a cross-sectional area of the optical fiber, the cross-section being orthogonal to a longitudinal axis of the optical fiber. In some examples, the optical fiber distal portion 600 can have a uniform refractive index. The therapeutic light and the illumination light emerging from the core can expand radially in a cone as it propagates distal in the in the optical fiber distal portion 600 to strike the dichroic thin-film coating 602.

In some of these examples, in which the dichroic thin-film coating 602 can reflect at least some of the therapeutic light and transmit at least some of the illumination light, the wavelength-sensitive light separator can further include a light redirector 606 that can redirect the transmitted illumination light. In the absence of such a light redirector 606, the illumination light that has transmitted through the dichroic thin-film coating 602 could be retained inside the optical fiber distal portion 600, because the illumination light could strike the exterior of the optical fiber distal portion 600 at an incident angle greater than the critical angle and could therefore experience total internal reflection that could keep the illumination light within the optical fiber distal portion 600. The light redirector 606 can violate the condition of total internal reflection and can therefore couple some or all of the illumination light out of the optical fiber distal portion 600.

The dichroic thin-film coating 602 can be disposed between a central (e.g., interior) portion of the optical fiber distal portion 600 and the light redirector 606. To space apart the dichroic thin-film coating 602 from the light redirector 606, the optical fiber distal portion 600 can include an optional spacer layer.

Figure 7:
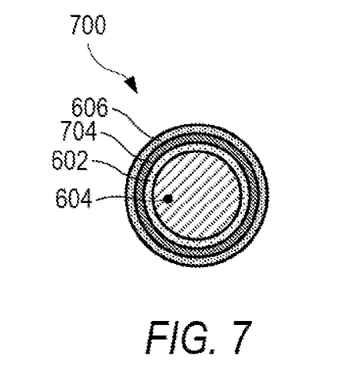
FIG. 7 shows an end-on cross-sectional view of an example of an optical fiber distal portion.

FIG. 7 shows an end-on cross-sectional view of an example of an optical fiber distal portion 700. In the configuration of FIG. 7, the dichroic thin-film coating 602 can be disposed on a circumferential edge of the optical fiber distal portion 700, a spacer layer 704 can be disposed on the dichroic thin-film coating 602, and the light redirector 606 can be disposed on the spacer layer 704. Other suitable configurations can also be used.

In some examples, the light redirector 606 can include a light scatterer, such as a textured surface or a roughened surface. The textured surface can diffuse the illumination light by imparting random propagation directions to light rays that strike the textured surface. The random propagation directions can violate the condition of total internal reflection, such that the textured surface can couple some or all of the illumination light out of the optical fiber distal portion 600 or optical fiber distal portion 700. Note that the dichroic thin-film coating 602 can prevent all or most of the therapeutic light from striking the textured surface, so that the textured surface couples out only or mostly illumination light from the distal portion 600 or distal portion 700 of the optical fiber.

In some examples, the light redirector 606 can include a diffraction grating. The diffraction grating can couple at least some of the illumination light into a diffracted order, such as the negative first diffracted order, to couple some or all of the illumination light out of the optical fiber distal portion 600 or optical fiber distal portion 700. The diffraction grating can include diffraction features (e.g., grating lines) that are substantially orthogonal to the longitudinal axis of the optical fiber. In some examples, the diffraction features can have a feature depth selected to raise a diffraction efficiency of the negative first order (or negative second order, or another suitable non-zero order) for the illumination light. The diffraction features or grating lines can be spaced apart (e.g., evenly spaced) with a grating pitch. The grating pitch can be selected such that illumination light incident on the diffraction grating with an angle of incidence greater than the critical angle can couple into a negative first (or other suitable) diffracted order. For example, the grating pitch can be selected such that the diffracted order can propagate in free space away from the distal portion of the optical fiber at a suitable angle, such as an angle that allows the illumination light to progress toward the target as it propagates away from a longitudinal axis of the optical fiber. Such a suitable grating pitch can be calculated from the well-known grating equation. Note that the dichroic thin-film coating 602 can prevent all or most of the therapeutic light from striking the diffraction grating, so that the diffraction grating couples out only or mostly illumination light from the optical fiber distal portion 600 or optical fiber distal portion 700.

In some examples, the functions of the wavelength-sensitive light separator and the light redirector can be combined into a single diffraction grating. Such a dual-function diffraction grating can be disposed on the lateral side of the optical fiber at the distal portion of the optical fiber. Unlike the configuration described above, the dual-function diffraction grating can receive both illumination light (in the visible portion of the electromagnetic spectrum) and the therapeutic light (in the infrared portion of the electromagnetic spectrum). The diffraction grating can reflect at least some of the therapeutic light and transmit at least some of the illumination light. This dual-function diffraction grating can have diffraction features spaced apart by a feature spacing. The feature spacing can be selected such that at least some of the illumination light transmits through the diffraction grating in a negative first order in transmission and such that the therapeutic light does not produce any diffracted orders. Such a feature spacing can be determined from applying the grating equation twice, once for a wavelength of the illumination light and once for a wavelength of the therapeutic light. In some examples, the diffraction features can be arranged orthogonal to a longitudinal axis of the optical fiber. In some examples, the diffraction features can have a feature depth selected to raise a diffraction efficiency of the negative first order for the illumination light.

In the configurations of FIGS. 2-7, described in detail above, the optical fiber can include a single core. The therapeutic light and the illumination light can propagate, together, along the single core of the optical fiber to the distal portion of the optical fiber. At the distal portion, the wavelength-sensitive light separator can separate the therapeutic light and the illumination light.

In the configurations of FIGS. 8-11, described in detail below, the optical fiber can include multiple cores. The therapeutic light and the illumination light can propagate, separately, along the different cores of the optical fiber to the distal portion of the optical fiber. At the distal portion, the optical fiber can be configured to direct the illumination light (from the core that guides the illumination light) to exit the optical fiber circumferentially through a lateral side of the optical fiber. For example, the cladding can be thinned and/or textured proximate the core of the illumination light, to allow the illumination light to exit the optical fiber circumferentially through the lateral side of the optical fiber. The cladding may not be thinned and/or textured proximate the core that guides the therapeutic light, so that the therapeutic light can exit the optical fiber longitudinally through the distal end of the optical fiber.

The endoscope can include an optical fiber that can direct therapeutic light and illumination light longitudinally along the optical fiber to a distal portion of the endoscope. The therapeutic light and the illumination light can have different wavelengths.

Figure 8:
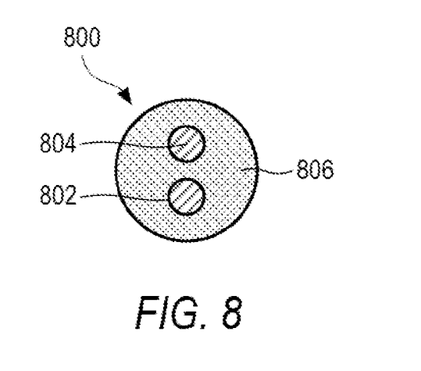
FIG. 8 shows an end-on cross-sectional view of an example of an optical fiber that includes multiple cores.

FIG. 8 shows an end-on cross-sectional view of an example of an optical fiber 800 that includes multiple cores 802, 804. The optical fiber 800 can include a first core 802 that can direct the therapeutic light to the distal portion of the endoscope. The optical fiber 800 can direct the therapeutic light to exit the optical fiber 800 longitudinally through a distal end of the optical fiber 800. The optical fiber 800 can include a second core 804 that can direct the illumination light to the distal portion of the endoscope. The optical fiber 800 can direct the illumination light to exit the optical fiber 800 circumferentially through a lateral side of the optical fiber 800 at a distal portion of the optical fiber 800.

In some examples, the first core 802 and the second core 804 can extend generally longitudinally along the optical fiber 800. For example, the first core 802 and the second core 804 can both be generally parallel to the longitudinal axis of the optical fiber 800. As another example, the first core 802 and the second core 804 can both precess helically around the longitudinal axis of the optical fiber 800.

In some examples, the first core 802 and the second core 804 can be formed from a material having a first refractive index. The optical fiber 800 can include a cladding 806 that surrounds the first core 802 and the second core 804. The cladding 806 can be formed from a cladding material having a second refractive index that is less than the first refractive index. The cladding 806 can be sized to isolate the therapeutic light from the second core and isolate the illumination light from the first core. For example, the first core 802 can define a first propagation mode having a first mode size, the second core 804 can define a second propagation mode having a second mode size, and the cladding 806 can space the first core 802 apart from the second core 804 by a distance greater than a sum of the first mode size and the second mode size.

Figure 9:
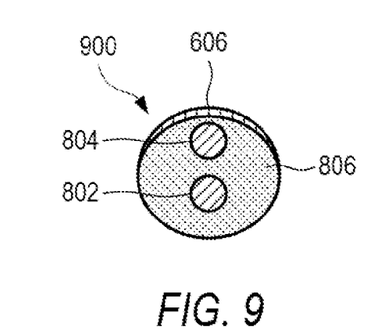
FIG. 9 shows an end-on cross-sectional view of an example of an optical fiber distal portion for the optical fiber of FIG. 8.

In a distal portion of the optical fiber 800, the cladding 806 can be thinned proximate the second core 804 to extract light from the second core 804 but not the first core 802. FIG. 9 shows an end-on cross-sectional view of an example of an optical fiber distal portion 900 for the optical fiber 800 of FIG. 8.

The cladding 806 can be thinned in a region proximate the second core 804, to allow light in the second core 804 to be directed onto a light redirector 606. As a specific example, proximate a midpoint between the distal portion of the optical fiber 800 and a proximal portion of the optical fiber 800, the second core 804 can be spaced apart from an outer edge of the cladding 806 by a first separation. At the distal portion of the optical fiber 800, the second core 804 can be spaced apart from the outer edge of the cladding 806 by a second separation that is less than the first separation. In some of these examples, the second separation can be selected such that a propagation mode of the illumination light extends to the outer edge of the cladding 806 at the distal portion of the optical fiber 800. At least a portion of the illumination light can exit the optical fiber 800 at the distal portion of the optical fiber 800.

To direct the illumination light out of the optical fiber 800, the optical fiber can include a light redirector 606, such as a textured surface, which can violate the condition of total internal reflection and can therefore couple some or all of the illumination light out of the distal portion of the optical fiber 800. The light redirector 606 has been described in detail above.

Figure 10:
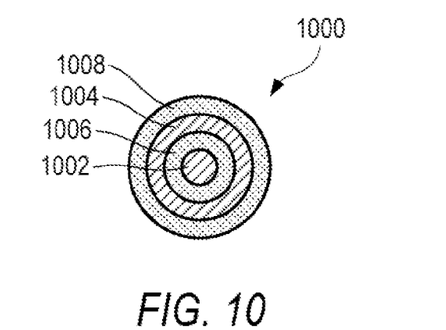
FIG. 10 shows an end-on cross-sectional view of an example of an optical fiber that includes multiple cores.

FIG. 10 shows an end-on cross-sectional view of an example of an optical fiber 1000 that includes multiple cores 1002, 1004. The optical fiber 1000 can include a first core 1002 that can direct the therapeutic light to the distal portion of the endoscope. The optical fiber 1000 can direct the therapeutic light to exit the optical fiber 1000 longitudinally through a distal end of the optical fiber 1000. The optical fiber 1000 can include a second core 1004 that can direct the illumination light to the distal portion of the endoscope. The optical fiber 1000 can direct the illumination light to exit the optical fiber 1000 circumferentially through a lateral side of the optical fiber 1000 at a distal portion of the optical fiber 1000.

In the configuration of FIG. 10, the first core 1002 can extend along a longitudinal axis of the optical fiber 1000. The second core 1004 can extend cylindrically around the first core 1002. The first core 1002 and the second core 1004 can be formed from a material having a first refractive index. The optical fiber 1000 can includes an interior cladding 1006 disposed between the first core 1002 and the second core 1004. The interior cladding 1006 can be formed from a cladding material having a second refractive index that is less than the first refractive index. The interior cladding 1006 can be sized to isolate the therapeutic light from the second core 1004 and isolate the illumination light from the first core 1002. The optical fiber 1000 can include an exterior cladding 1008 that surrounds the second core 1004. The exterior cladding 1008 can be formed from the cladding material.

Figure 11:
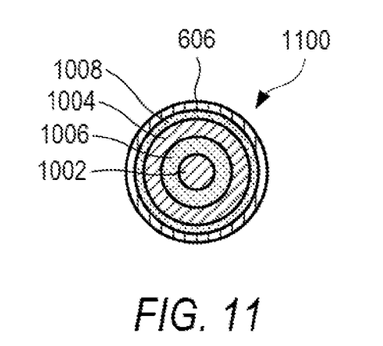
FIG. 11 shows an end-on cross-sectional view of an example of an optical fiber distal portion for the optical fiber of FIG. 10.

In a distal portion of the optical fiber 1000, the exterior cladding 1008 can be thinned to extract light from the second core 1004 but not the first core 1002. FIG. 11 shows an end-on cross-sectional view of an example of an optical fiber distal portion 1100 for the optical fiber 1000 of FIG. 10.

The exterior cladding 1008 can be thinned in a region proximate the second core 1004, to allow light in the second core 1004 to be directed onto a light redirector 606, such as a textured surface. As a specific example, the exterior cladding 1008 can have a first thickness proximate a midpoint between the distal portion of the optical fiber 1000 and a proximal portion of the optical fiber 1000. The exterior cladding 1008 can have a second thickness at the distal portion of the optical fiber 1000. The second thickness can be less than the first thickness. The second thickness can be selected such that a propagation mode of the illumination light extends to an outer edge of the exterior cladding 1008 at the distal portion of the optical fiber 1000. At least a portion of the illumination light can exit the optical fiber 1000 at the distal portion of the optical fiber 1000.

To direct the illumination light out of the optical fiber 1000, the optical fiber can include a light redirector 606, such as a textured surface, which can violate the condition of total internal reflection and can therefore couple some or all of the illumination light out of the distal portion of the optical fiber 1000. The light redirector 606 has been described in detail above. As a specific example, the exterior cladding 1008 can have a textured outer edge at the distal portion of the optical fiber 1000. The textured outer edge can direct at least some of the illumination light out of the optical fiber 1000 at the distal portion of the optical fiber 1000.

Figure 12:
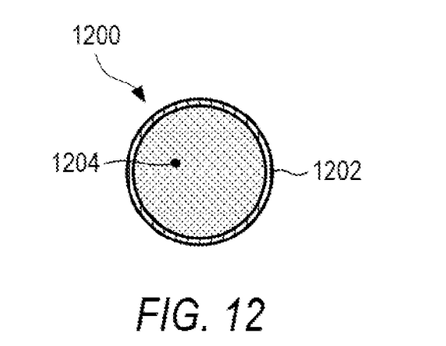
FIG. 12 shows an end-on cross-sectional view of an example of an optical fiber distal portion.

As a specific example, FIG. 12 shows an end-on cross-sectional view of an example of an optical fiber distal portion 1200. The optical fiber distal portion 1200 can be used with the optical fiber 118 in the endoscope 100 of FIG. 1.

The endoscope 100 can include the elongated endoscope body 102. The optical fiber 118 can extend along the endoscope body 102. The optical fiber 118 can be a multi-mode optical fiber 118. The optical fiber 118 can include a core 202 (FIG. 2) surrounded by a cladding 206 (FIG. 2). The core 202 and the cladding 206 can have different refractive indices. The core 202 can guide therapeutic light 116 and illumination light 120 longitudinally along the optical fiber 118 as guided light to a distal portion of the endoscope body 102. The therapeutic light can have a greater wavelength than the illumination light. The optical fiber 118 can include an optical fiber distal portion 1200 formed from a material 1204 that has a substantially uniform refractive index. The optical fiber distal portion 1200 can receive the guided light and propagate the guided light distally within the optical fiber distal portion 1200 as unguided light. The unguided light can expand radially as it propagates distally within the optical fiber distal portion 1200 to strike a lateral side of the optical fiber distal portion 1200. A diffraction grating 1202 can be disposed on the lateral side of the optical fiber distal portion 1200. The diffraction grating 1202 can have a grating pitch selected such that the following two conditions occur. First, the diffraction grating 1202 can couple at least some of the illumination light 120 out of the optical fiber distal portion 1200 into a negative diffracted order, such as the negative first diffractive order. Second, the diffraction grating 1202 may not couple the therapeutic light 116 into a diffracted order. (For example, compared to a wavelength of the therapeutic light 116, the grating pitch may be too small to produce any non-zero diffracted orders for the therapeutic light 116. Such a condition is described mathematically by the well-known grating equation.) As a result, the therapeutic light 116 can reflect from the diffraction grating 1202 to remain in the optical fiber distal portion 1200 and exit the optical fiber distal portion 1200 through a distal end of the optical fiber 118.

FIG. 13 shows a cross-sectional side view of an example of a distal portion 1300 of an optical fiber 1302, suitable for use in the endoscope 100 of FIG. 1. FIG. 14 shows an end-on view of a distal end 1314 of the optical fiber 1302 of FIG. 13.

The endoscope 100 can include an elongated endoscope body 102 (FIG. 1). The optical fiber 1302 can extend along the endoscope body 102. The optical fiber 1302 can direct therapeutic light and illumination light longitudinally along the optical fiber 1302 to a distal portion of the endoscope body 102. The therapeutic light and the illumination light can have different wavelengths A wavelength-sensitive light separator can be disposed at a distal portion of the optical fiber 1302. The wavelength-sensitive light separator can direct the illumination light to exit the optical fiber 1302 laterally through a lateral side of the optical fiber 1302 at the distal portion of the optical fiber 1302. The wavelength-sensitive light separator can permit the therapeutic light to exit the optical fiber 1302 longitudinally through a distal end 1314 of the optical fiber 1302.

In some examples, the wavelength-sensitive light separator can include a fiber Bragg grating 1304A disposed along a length of the distal portion of the optical fiber 1302. The fiber Bragg grating 1304A can be formed from periodic and/or aperiodic variations in the refractive index of the fiber core 1306. Each transition between a relatively low refractive index and a relatively high refractive index can produce a reflection in the fiber core 1306. The reflections can interfere with one another. For wavelengths at which the reflections are in phase with one another, such as a central wavelength, the fiber Bragg grating 1304A can produce a relatively large reflection in the fiber core 1306. For wavelengths at which the reflections are not in phase with one another, such as wavelengths away from the central wavelength, the reflected light in the fiber core 1306 is relatively small. The Bragg grating 1304A can function as a wavelength-sensitive filter, which can reflect light relatively strongly at a central wavelength and can reflect light relatively weakly away from the central wavelength. The central wavelength can be determined by an effective refractive index of the core and the grating period (e.g., an on-axis spacing of adjacent grating features 1308). The bandwidth of the reflection (e.g., a spectral width of the reflected peak, in units of wavelength) can be determined by the central wavelength, the difference between the relatively high refractive index and the relatively low refractive index, and a fraction of optical power that is contained in the fiber core 1306.

For configurations in which the grating features 1308 of the fiber Bragg grating 1304A are formed orthogonally with respect to a longitudinal axis (LA) of the optical fiber 1302, the reflections from the fiber Bragg grating 1304A remain in the fiber core 1306, and traverse the optical fiber 1302 in the opposite direction of the incident light (e.g., propagating proximally away from the distal end 1314 of the optical fiber 1302).

To configure the fiber Bragg grating 1304A to direct the reflected light out of the optical fiber 1302 laterally, such as through a lateral edge of the fiber, the grating features 1308 of the fiber Bragg grating 1304A can be arranged at an oblique angle (e.g., non-orthogonal) with respect to the longitudinal axis (LA) of the optical fiber 1302. Specifically, the grating features 1308 of the fiber Bragg grating 1304A, such as planar interfaces between the relatively high refractive index and the relatively low refractive index) can be angled at a non-orthogonal angle with respect to the longitudinal axis (LA) of the optical fiber 1302. This oblique angling can direct the reflected light out of the fiber core 1306, through the fiber cladding 1310, and out of the optical fiber 1302 through the lateral side of the optical fiber 1302.

In some examples, the fiber Bragg grating 1304A can include an obliquely-angled fiber Bragg grating 1304A. The obliquely-angled fiber Bragg grating 1304A can reflect therefrom at least a spectral portion of the illumination light to form reflected light portion 1312A. The reflected light portion 1312A can be in a visible portion of the electromagnetic spectrum. The obliquely-angled fiber Bragg grating 1304A can transmit therethrough the therapeutic light 116. The therapeutic light 116 can be in an infrared portion of the electromagnetic spectrum.

In some examples, the wavelength-sensitive light separator can include a plurality of obliquely-angled fiber Bragg gratings 1304A, 1304B, 1304C, and 1304D, disposed sequentially along a length of the distal portion of the optical fiber 1302. Using sequential obliquely-angled fiber Bragg gratings 1304A, 1304B, 1304C, and 1304D can allow the illumination light to be directed out of the optical fiber 1302 in multiple reflected light portions 1312A, 1312B, 1312C, and 1312D. Using multiple reflected portions can optionally provide greater flexibility than reflecting all of the illumination light out of the optical fiber 1302 in a single reflected light portion.

In some examples, an individual obliquely-angled fiber Bragg grating of the plurality of obliquely-angled fiber Bragg gratings 1304A, 1304B, 1304C, and 1304D can reflect a respective reflected light portions 1312A, 1312B, 1312C, or 1312D of the illumination light out of the fiber core 1306, through the fiber cladding 1310, and out of the optical fiber 1302 through the lateral side of the optical fiber 1302.

In some examples, at least two obliquely-angled fiber Bragg gratings of the plurality of obliquely-angled fiber Bragg gratings 1304A, 1304B, 1304C, and 1304D can have different grating pitches. Because the grating pitch at least in part determines the central wavelength that is reflected by the fiber Bragg grating, using two gratings having different pitches can allow the optical fiber 1302 to reflect different spectral portions of the illumination light into different reflected light portions. For example, at least two obliquely-angled fiber Bragg gratings of the plurality of obliquely-angled fiber Bragg gratings 1304A, 1304B, 1304C, and 1304D can reflect different spectral portions of the illumination light. Specifically, the optical fiber 1302 can reflect a first spectral portion of the illumination light into a first reflected light portion 1312A, and a second spectral portion of the illumination light into a first reflected light portion 1312B. Using multiple spectral portions can allow the optical fiber 1302 to use multiple fiber Bragg gratings of a relatively small bandwidth to cover the spectral width of the illumination light. Fiber Bragg gratings with relatively small bandwidths may be easier to manufacture than a single fiber Bragg grating having a relatively large bandwidth that covers the full spectral width of the illumination light.

In some examples, at least two obliquely-angled fiber Bragg gratings of the plurality of obliquely-angled fiber Bragg gratings 1304A, 1304B, 1304C, and 1304D can have a same grating pitch. Using the same grating pitch for two or more fiber Bragg gratings can allow the corresponding reflected portions to have a same central wavelength. For example, by varying the refractive index differences from grating-to-grating to control peak reflectance values of the fiber Bragg gratings, the fiber can direct a same fractional amount of one spectral portion of the illumination light into multiple reflected light portions.

In some examples, at least two obliquely-angled fiber Bragg gratings of the plurality of obliquely-angled fiber Bragg gratings 1304A, 1304B, 1304C, and 1304D can be oriented at different azimuthal positions around a longitudinal axis (LA) of the optical fiber 1302, such that the respective reflected portions 1312A, 1312B, 1312C, and 1312D of the illumination light emerge from the optical fiber 1302 at the different azimuthal positions. The example of FIG. 14 shows four reflected portions 1312A, 1312B, 1312C, and 1312D emerging at different azimuthal positions that are equally spaced apart by 90 degrees around the circumference of the optical fiber 1302. Other azimuthal positions and other numbers of fiber Bragg gratings and reflected portions can also be used. The end-on view of FIG. 14 shows only the azimuthal positions; it will be understood that the true propagation directions for the reflected portions 1312A, 1312B, 1312C, and 1312D include a propagation component toward the viewer in FIG. 14, such that a distance between the reflected portion and the longitudinal axis (LA) increases as the reflected portion propagates in the positive-Z direction (e.g., toward the viewer).

In some examples, at least two obliquely-angled fiber Bragg gratings of the plurality of obliquely-angled fiber Bragg gratings 1304A, 1304B, 1304C, and 1304D can be obliquely angled at different angles, such that the respective reflected portions 1312A, 1312B, 1312C, and 1312D of the illumination light can emerge from the optical fiber 1302 at different propagation angles θ with respect to the longitudinal axis (LA) of the optical fiber 1302. Using different propagation angles θ can allow the optical fiber 1302 to direct the reflected portions 1312A, 1312B, 1312C, and 1312D of the illumination light to illuminate a same location of a target, or to illuminate a particularly large area of the target or a particularly small area of the target, as needed.

In some examples, the obliquely-angled fiber Bragg gratings of the plurality of obliquely-angled fiber Bragg gratings 1304A, 1304B, 1304C, and 1304D can transmit therethrough the therapeutic light 116. For example, an obliquely-angled fiber Bragg grating can be relatively highly reflective for a central wavelength in the visible portion of the electromagnetic spectrum, so as to reflect all or a portion of the illumination light, and can have be relatively highly transmissive for an infrared portion of the electromagnetic spectrum, so as to transmit all or a portion of the therapeutic light 116. In some examples, each obliquely-angled fiber Bragg grating of the plurality of obliquely-angled fiber Bragg gratings 1304A, 1304B, 1304C, and 1304D can reflect therefrom a respective spectral portion of the illumination light, the illumination light being in a visible portion of the electromagnetic spectrum. In some examples, each obliquely-angled fiber Bragg grating of the plurality of obliquely-angled fiber Bragg gratings 1304A, 1304B, 1304C, and 1304D can transmit therethrough the therapeutic light 116, the therapeutic light 116 being in an infrared portion of the electromagnetic spectrum.

Figure 15:
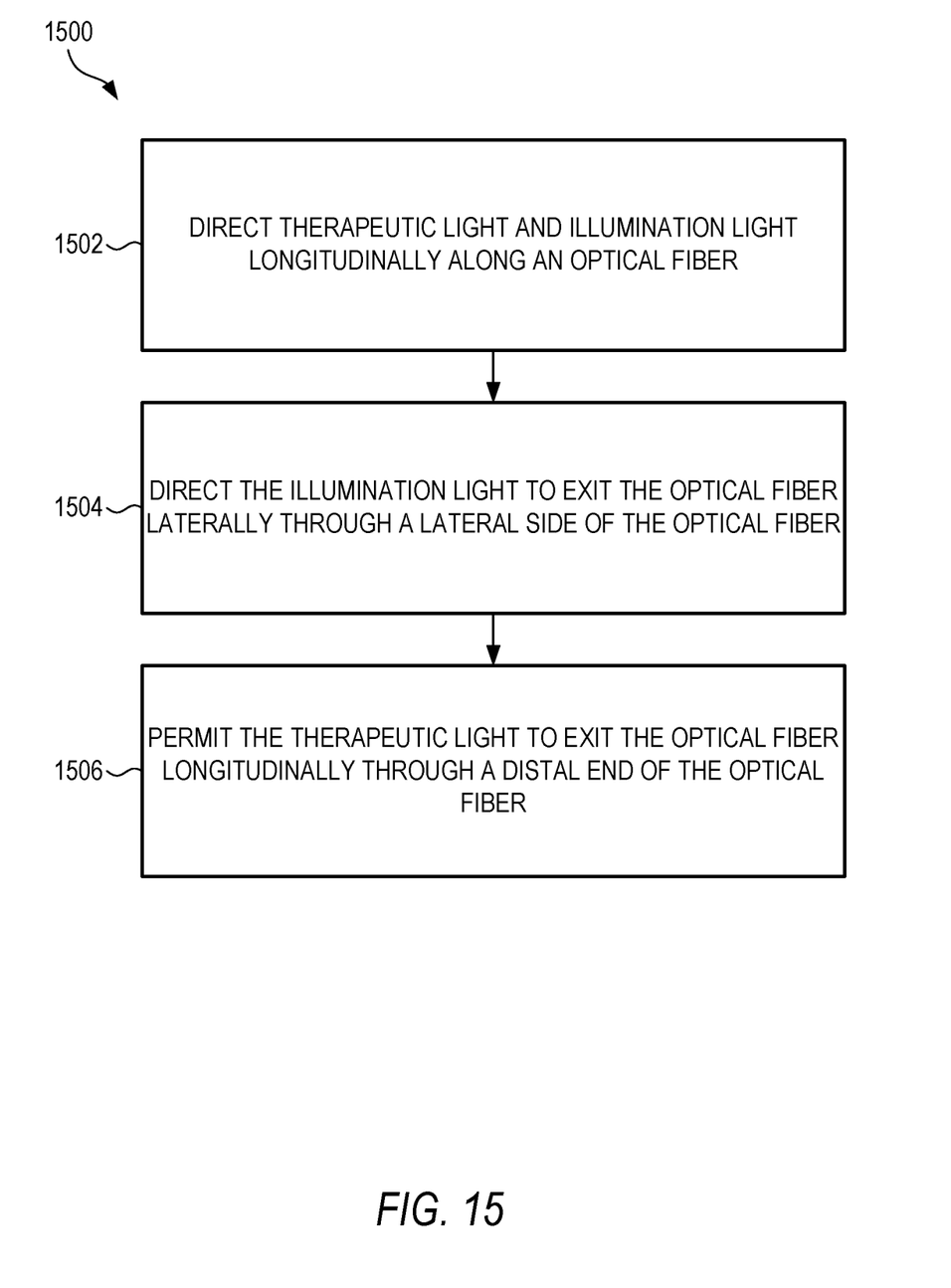
FIG. 15 shows an example of a method for delivering light in an endoscope.

FIG. 15 shows an example of a method 1500 for delivering light in an endoscope. The method can be executed by an endoscope that includes the optical fiber configurations shown in FIGS. 1-14, or by any suitable endoscope. The method 1500 is but one example of a method for delivering light in an endoscope. Other suitable methods can also be used.

At operation 1502, an endoscope can direct therapeutic light and illumination light longitudinally along an optical fiber to a distal portion of an elongated endoscope body. The therapeutic light and the illumination light can have different wavelengths.

At operation 1504, the endoscope can direct, with a wavelength-sensitive light separator, the illumination light to exit the optical fiber laterally through a lateral side of the optical fiber at the distal portion of the optical fiber.

At operation 1506, the endoscope can permit, with the wavelength-sensitive light separator, the therapeutic light to exit the optical fiber longitudinally through a distal end of the optical fiber.

In some examples, the wavelength-sensitive light separator can include a fiber Bragg grating disposed along a length of the distal portion of the optical fiber. In some examples, directing the illumination light to exit the optical fiber can include reflecting, with the fiber Bragg grating, at least some of the illumination light out of a core of the optical fiber, through a cladding of the optical fiber, and out of the optical fiber through the lateral side of the optical fiber.

In some examples, the wavelength-sensitive light separator can include a plurality of obliquely-angled fiber Bragg gratings disposed sequentially along a length of the distal portion of the optical fiber. In some examples, directing the illumination light to exit the optical fiber can include reflecting, with each obliquely-angled fiber Bragg grating of the plurality of obliquely-angled fiber Bragg gratings, a respective portion of the illumination light out of a core of the optical fiber, through a cladding of the optical fiber, and out of the optical fiber through the lateral side of the optical fiber.

In some examples, the wavelength-sensitive light separator can include a length of coreless fiber disposed at the distal portion of the optical fiber and a diffraction grating disposed on the lateral edge of the coreless fiber. In some examples, directing the illumination light to exit the optical fiber can include directing the therapeutic light and the illumination light to emerge from a core of the optical fiber into the coreless fiber; propagating the therapeutic light and the illumination light to expand radially in a cone in the coreless fiber to strike the lateral edge of the coreless fiber and strike the diffraction grating; reflecting, with the diffraction grating, at least some of the therapeutic light; and transmitting, with the diffraction grating, at least some of the illumination light.

EXAMPLES

To further illustrate the device, related system, and/or related method discussed herein, a non-limiting list of examples is provided below. Each of the following non-limiting examples can stand on its own or can be combined in any permutation or combination with any one or more of the other examples.

In Example 1, an endoscope can include: an elongated endoscope body; and an optical fiber extending along the endoscope body, the optical fiber configured to direct therapeutic light and illumination light longitudinally along the optical fiber to a distal portion of the endoscope body, the therapeutic light and the illumination light having different wavelengths, the endoscope including a wavelength-sensitive light separator disposed at a distal portion of the optical fiber and configured to: direct the therapeutic light to exit the optical fiber longitudinally through a distal end of the optical fiber; and direct the illumination light to exit the optical fiber circumferentially through a lateral side of the optical fiber at the distal portion of the optical fiber.

In Example 2, the endoscope of Example 1 can optionally be configured such that the wavelength-sensitive light separator includes a dichroic thin-film coating disposed on the lateral side of the optical fiber at the distal portion of the optical fiber, the dichroic thin-film coating configured to reflect at least some of the therapeutic light and transmit at least some of the illumination light.

In Example 3, the endoscope of any one of Examples 1-2 can optionally be configured such that the optical fiber includes: a core extending along a length of the optical fiber, the core being formed from a core material having a core refractive index; and a cladding surrounding the core along the length of the optical fiber, the cladding being formed from a cladding material having a cladding refractive index that is less than the core refractive index; and wherein the distal portion of the optical fiber is formed from a material having a refractive index that is invariant over a cross-sectional area of the optical fiber, the cross-section being orthogonal to a longitudinal axis of the optical fiber, such that the therapeutic light and the illumination light emerging from the core expands radially in a cone in the distal portion to strike the dichroic thin-film coating.

In Example 4, the endoscope of any one of Examples 1-3 can optionally be configured such that the optical fiber includes: a core extending along a length of the optical fiber, the core being formed from a core material having a core refractive index; and a cladding surrounding the core along the length of the optical fiber, the cladding being formed from a cladding material having a cladding refractive index that is less than the core refractive index; and the cladding has a first thickness proximate a midpoint between the distal portion of the optical fiber and a proximal portion of the optical fiber; and the cladding has a second thickness at the distal portion of the optical fiber, the second thickness being less than the first thickness.

In Example 5, the endoscope of any one of Examples 1-4 can optionally be configured such that the wavelength-sensitive light separator includes a diffraction grating disposed on the lateral side of the optical fiber at the distal portion of the optical fiber, the diffraction grating configured to reflect at least some of the therapeutic light and transmit at least some of the illumination light.

In Example 6, the endoscope of any one of Examples 1-5 can optionally be configured such that the diffraction grating has diffraction features spaced apart by a feature spacing, the feature spacing being selected such that at least some of the illumination light transmits through the diffraction grating in a negative first order in transmission and such that the therapeutic light does not produce any diffracted orders.

In Example 7, the endoscope of any one of Examples 1-6 can optionally be configured such that the diffraction features are arranged orthogonal to a longitudinal axis of the optical fiber.

In Example 8, the endoscope of any one of Examples 1-7 can optionally be configured such that the diffraction features have a feature depth selected to raise a diffraction efficiency of the negative first order for the illumination light.

In Example 9, the endoscope of any one of Examples 1-8 can optionally be configured such that the optical fiber includes: a core extending along a length of the optical fiber, the core being formed from a core material having a core refractive index; and a cladding surrounding the core along the length of the optical fiber, the cladding being formed from a cladding material having a cladding refractive index less than the core refractive index; and wherein the distal portion of the optical fiber is formed from a material having a refractive index that is invariant over a cross-sectional area of the optical fiber, the cross-section being orthogonal to a longitudinal axis of the optical fiber, such that the therapeutic light and the illumination light emerging from the core expands radially in a cone in the distal portion to strike the wavelength-sensitive light separator.

In Example 10, the endoscope of any one of Examples 1-9 can optionally be configured such that the illumination light has at least one wavelength between 400 nm and 700 nm.

In Example 11, the endoscope of any one of Examples 1-10 can optionally be configured such that the illumination light includes a continuum of wavelengths, at least a portion of the continuum of wavelengths being between 400 nm and 700 nm.

In Example 12, the endoscope of any one of Examples 1-11 can optionally be configured such that the therapeutic light has a wavelength in the infrared portion of the electromagnetic spectrum.

In Example 13, the endoscope of any one of Examples 1-12 can optionally be configured such that the therapeutic light has a wavelength corresponding to an emission wavelength of a pulsed thulium laser.

In Example 14, the endoscope of any one of Examples 1-13 can optionally be configured such that the therapeutic light has a wavelength between 1810 nm and 2100 nm.

In Example 15, the endoscope of any one of Examples 1-14 can optionally be configured such that the therapeutic light has a wavelength of about 1940 nm.

In Example 16, a method for delivering light in an endoscope can include: directing therapeutic light and illumination light longitudinally along an optical fiber to a distal portion of an endoscope, the therapeutic light and the illumination light having different wavelengths; directing the therapeutic light to exit the optical fiber longitudinally through a distal end of the optical fiber; and directing the illumination light to exit the optical fiber circumferentially through a lateral side of the optical fiber at a distal portion of the optical fiber.

In Example 17, the method of Example 16 can optionally further include: directing the therapeutic light and the illumination light onto a wavelength-sensitive light separator disposed at the distal portion of the optical fiber; reflecting the therapeutic light from the wavelength-sensitive light separator to toward the distal end of the optical fiber; and transmitting the illumination light through the wavelength-sensitive light separator to exit the optical fiber circumferentially through the lateral side of the optical fiber.

In Example 18, the method of any one of Examples 16-17 can optionally be configured such that the wavelength-sensitive light separator includes a dichroic thin-film coating disposed on the lateral side of the optical fiber at the distal portion of the optical fiber, the dichroic thin-film coating configured to reflect at least some of the therapeutic light and transmit at least some of the illumination light.

In Example 19, the method of any one of Examples 16-18 can optionally be configured such that the wavelength-sensitive light separator includes a diffraction grating disposed on the lateral side of the optical fiber at the distal portion of the optical fiber, the diffraction grating configured to reflect at least some of the therapeutic light and transmit at least some of the illumination light.

In Example 20, an endoscope can include: an elongated endoscope body; an optical fiber extending along the endoscope body, the optical fiber being a multi-mode optical fiber and including a core surrounded by a cladding, the core and the cladding having different refractive indices, the core configured to guide therapeutic light and illumination light longitudinally along the optical fiber as guided light to a distal portion of the endoscope body, the therapeutic light having a greater wavelength than the illumination light, the optical fiber including an optical fiber distal portion having a substantially uniform refractive index, the optical fiber distal portion being configured to receive the guided light and propagate the guided light distally within the optical fiber distal portion as unguided light, the unguided light configured to expand radially as it propagates distally within the optical fiber distal portion to strike a lateral side of the optical fiber distal portion; and a diffraction grating disposed on the lateral side of the optical fiber distal portion, the diffraction grating having a grating pitch selected such that: the diffraction grating couples at least some of the illumination light out of the optical fiber distal portion into a negative diffracted order; and the diffraction grating does not couple the therapeutic light into a diffracted order.

In Example 21, an endoscope can include: an elongated endoscope body; and an optical fiber extending along the endoscope body, the optical fiber configured to direct therapeutic light and illumination light longitudinally along the optical fiber to a distal portion of the endoscope body, the therapeutic light and the illumination light having different wavelengths, the optical fiber including a first core configured to direct the therapeutic light to the distal portion of the endoscope, the optical fiber being configured to direct the therapeutic light to exit the optical fiber longitudinally through a distal end of the optical fiber, the optical fiber including a second core configured to direct the illumination light to the distal portion of the endoscope, the optical fiber being further configured to direct the illumination light to exit the optical fiber circumferentially through a lateral side of the optical fiber at a distal portion of the optical fiber.

In Example 22, the endoscope of Example 21 can optionally be configured such that the first core extends along a longitudinal axis of the optical fiber; and the second core extends cylindrically around the first core.

In Example 23, the endoscope of any one of Examples 21-22 can optionally be configured such that: the first core and the second core are formed from a material having a first refractive index; and the optical fiber includes an interior cladding disposed between the first core and the second core, the interior cladding being formed from a cladding material having a second refractive index that is less than the first refractive index.

In Example 24, the endoscope of any one of Examples 21-23 can optionally be configured such that the interior cladding is sized to isolate the therapeutic light from the second core and isolate the illumination light from the first core.

In Example 25, the endoscope of any one of Examples 21-24 can optionally be configured such that: the optical fiber includes an exterior cladding surrounding the second core, the exterior cladding being formed from the cladding material.

In Example 26, the endoscope of any one of Examples 21-25 can optionally be configured such that: the exterior cladding has a first thickness proximate a midpoint between the distal portion of the optical fiber and a proximal portion of the optical fiber; and the exterior cladding has a second thickness at the distal portion of the optical fiber, the second thickness being less than the first thickness.

In Example 27, the endoscope of any one of Examples 21-26 can optionally be configured such that: the second thickness is selected such that a propagation mode of the illumination light extends to an outer edge of the exterior cladding at the distal portion of the optical fiber; and at least a portion of the illumination light exits the optical fiber at the distal portion of the optical fiber.

In Example 28, the endoscope of any one of Examples 21-27 can optionally be configured such that the exterior cladding has a textured outer edge at the distal portion of the optical fiber, the textured outer edge being configured to direct at least some of the illumination light out of the optical fiber at the distal portion of the optical fiber.

In Example 29, the endoscope of any one of Examples 21-28 can optionally be configured such that the first core and the second core extend generally longitudinally along the optical fiber.

In Example 30, the endoscope of any one of Examples 21-29 can optionally be configured such that: the first core and the second core are formed from a material having a first refractive index; and the optical fiber includes a cladding that surrounds the first core and the second core, the cladding being formed from a cladding material having a second refractive index that is less than the first refractive index.

In Example 31, the endoscope of any one of Examples 21-30 can optionally be configured such that the cladding is sized to isolate the therapeutic light from the second core and isolate the illumination light from the first core.

In Example 32, the endoscope of any one of Examples 21-31 can optionally be configured such that: proximate a midpoint between the distal portion of the optical fiber and a proximal portion of the optical fiber, the second core is spaced apart from an outer edge of the cladding by a first separation; at the distal portion of the optical fiber, the second core is spaced apart from the outer edge of the cladding by a second separation that is less than the first separation.

In Example 33, the endoscope of any one of Examples 21-32 can optionally be configured such that: the second separation is selected such that a propagation mode of the illumination light extends to the outer edge of the cladding at the distal portion of the optical fiber; and at least a portion of the illumination light exits the optical fiber at the distal portion of the optical fiber.

In Example 34, the endoscope of any one of Examples 21-33 can optionally be configured such that the illumination light has at least one wavelength between 400 nm and 700 nm.

In Example 35, the endoscope of any one of Examples 21-34 can optionally be configured such that the illumination light includes a continuum of wavelengths, at least a portion of the continuum of wavelengths being between 400 nm and 700 nm.

In Example 36, the endoscope of any one of Examples 21-35 can optionally be configured such that the therapeutic light has a wavelength in the infrared portion of the electromagnetic spectrum.

In Example 37, the endoscope of any one of Examples 21-36 can optionally be configured such that the therapeutic light has a wavelength corresponding to an emission wavelength of a pulsed thulium laser.

In Example 38, the endoscope of any one of Examples 21-37 can optionally be configured such that the therapeutic light has a wavelength between 1810 nm and 2100 nm.

In Example 39, the endoscope of any one of Examples 21-38 can optionally be configured such that the therapeutic light has a wavelength of about 1940 nm.

What is claimed is:

1. An endoscope, comprising:
an elongated endoscope body;
an optical fiber extending along the endoscope body, the optical fiber configured to direct therapeutic light and illumination light longitudinally along the optical fiber to a distal portion of the endoscope body, the therapeutic light and the illumination light having different wavelengths; and
a wavelength-sensitive light separator disposed at a distal portion of the optical fiber, the wavelength-sensitive light separator configured to direct the illumination light to exit the optical fiber laterally through a lateral side of the optical fiber at the distal portion of the optical fiber and permit the therapeutic light to exit the optical fiber longitudinally through a distal end of the optical fiber.

2. The endoscope of claim 1, wherein the wavelength-sensitive light separator includes a fiber Bragg grating disposed along a length of the distal portion of the optical fiber,
the fiber Bragg grating being configured to reflect at least some of the illumination light out of a core of the optical fiber, through a cladding of the optical fiber, and out of the optical fiber through the lateral side of the optical fiber.

3. The endoscope of claim 2, wherein the fiber Bragg grating includes an obliquely-angled fiber Bragg grating and is configured to:
reflect therefrom at least a spectral portion of the illumination light, the reflected light being in a visible portion of the electromagnetic spectrum; and
transmit therethrough the therapeutic light, the therapeutic light being in an infrared portion of the electromagnetic spectrum.

4. The endoscope of claim 1, wherein the wavelength-sensitive light separator includes a plurality of obliquely-angled fiber Bragg gratings disposed sequentially along a length of the distal portion of the optical fiber,
an individual obliquely-angled fiber Bragg grating of the plurality of obliquely-angled fiber Bragg gratings being configured to reflect a respective portion of the illumination light out of a core of the optical fiber, through a cladding of the optical fiber, and out of the optical fiber through the lateral side of the optical fiber.

5. The endoscope of claim 4, wherein at least two obliquely-angled fiber Bragg gratings of the plurality of obliquely-angled fiber Bragg gratings have different grating pitches.

6. The endoscope of claim 4, wherein at least two obliquely-angled fiber Bragg gratings of the plurality of obliquely-angled fiber Bragg gratings are configured to reflect different spectral portions of the illumination light.

7. The endoscope of claim 4, wherein at least two obliquely-angled fiber Bragg gratings of the plurality of obliquely-angled fiber Bragg gratings are oriented at different azimuthal positions around a longitudinal axis of the optical fiber, such that the respective reflected portions of the illumination light emerge from the optical fiber at the different azimuthal positions.

8. The endoscope of claim 7, wherein the at least two obliquely-angled fiber Bragg gratings of the plurality of obliquely-angled fiber Bragg gratings have a same grating pitch.

9. The endoscope of claim 4, wherein at least two obliquely-angled fiber Bragg gratings of the plurality of obliquely-angled fiber Bragg gratings are obliquely angled at different angles, such that the respective reflected portions of the illumination light emerge from the optical fiber at different propagation angles with respect to a longitudinal axis of the optical fiber.

10. The endoscope of claim 4, wherein the obliquely-angled fiber Bragg gratings of the plurality of obliquely-angled fiber Bragg gratings are configured to transmit therethrough the therapeutic light.

11. The endoscope of claim 4, wherein each obliquely-angled fiber Bragg grating of the plurality of obliquely-angled fiber Bragg gratings is configured to:
reflect therefrom a respective spectral portion of the illumination light, the illumination light being in a visible portion of the electromagnetic spectrum; and
transmit therethrough the therapeutic light, the therapeutic light being in an infrared portion of the electromagnetic spectrum.

12. The endoscope of claim 1, wherein the wavelength-sensitive light separator includes:
a length of coreless fiber disposed at the distal portion of the optical fiber, the length of coreless fiber allowing the therapeutic light and the illumination light that emerges from a core of the optical fiber to expand radially in a cone in the coreless fiber to strike a lateral edge of the coreless fiber; and
a diffraction grating disposed on the lateral edge of the coreless fiber, the diffraction grating configured to reflect at least some of the therapeutic light and transmit at least some of the illumination light.

13. The endoscope of claim 12, wherein the diffraction grating has diffraction features spaced apart by a feature spacing such that at least some of the illumination light transmits through the diffraction grating.

14. The endoscope of claim 13, wherein:
the feature spacing produces a negative first order in transmission for the illumination light; and
the feature spacing does not produce any diffracted orders for the therapeutic light.

15. A method for delivering light in an endoscope, the method comprising:
directing therapeutic light and illumination light longitudinally along an optical fiber to a distal portion of an elongated endoscope body, the therapeutic light and the illumination light having different wavelengths;
directing, with a wavelength-sensitive light separator, the illumination light to exit the optical fiber laterally through a lateral side of the optical fiber at the distal portion of the optical fiber; and
permitting, with the wavelength-sensitive light separator, the therapeutic light to exit the optical fiber longitudinally through a distal end of the optical fiber.

16. The method of claim 15, wherein:
the wavelength-sensitive light separator includes a fiber Bragg grating disposed along a length of the distal portion of the optical fiber; and
directing the illumination light to exit the optical fiber comprises:
reflecting, with the fiber Bragg grating, at least some of the illumination light out of a core of the optical fiber, through a cladding of the optical fiber, and out of the optical fiber through the lateral side of the optical fiber.

17. The method of claim 15, wherein:
the wavelength-sensitive light separator includes a plurality of obliquely-angled fiber Bragg gratings disposed sequentially along a length of the distal portion of the optical fiber; and
directing the illumination light to exit the optical fiber comprises:
reflecting, with each obliquely-angled fiber Bragg grating of the plurality of obliquely-angled fiber Bragg gratings, a respective portion of the illumination light out of a core of the optical fiber, through a cladding of the optical fiber, and out of the optical fiber through the lateral side of the optical fiber.

18. The method of claim 15, wherein:
the wavelength-sensitive light separator includes a length of coreless fiber disposed at the distal portion of the optical fiber and a diffraction grating disposed on the lateral edge of the coreless fiber; and directing the illumination light to exit the optical fiber comprises:
- directing the therapeutic light and the illumination light to emerge from a core of the optical fiber into the coreless fiber;
- propagating the therapeutic light and the illumination light to expand radially in a cone in the coreless fiber to strike the lateral edge of the coreless fiber and strike the diffraction grating;
- reflecting, with the diffraction grating, at least some of the therapeutic light; and
- transmitting, with the diffraction grating, at least some of the illumination light.

19. An endoscope, comprising:
an elongated endoscope body;
an optical fiber extending along the endoscope body, the optical fiber configured to direct infrared therapeutic light and visible illumination light longitudinally along the optical fiber to a distal portion of the endoscope body; and
an obliquely-angled fiber Bragg grating disposed along a length of the distal portion of the optical fiber, the obliquely-angled fiber Bragg grating configured to reflect at least some of the visible illumination light out of the optical fiber through a lateral side of the optical fiber and transmit the infrared therapeutic light through the obliquely-angled fiber Bragg grating to exit the optical fiber longitudinally through a distal end of the optical fiber.

20. The endoscope of claim 19, further comprising a plurality of obliquely-angled fiber Bragg gratings that includes the obliquely-angled fiber Bragg grating, the plurality of obliquely-angled fiber Bragg gratings being disposed sequentially along the length of the distal portion of the optical fiber, each obliquely-angled fiber Bragg grating of the plurality of obliquely-angled fiber Bragg gratings being configured to reflect a respective portion of the illumination light out of a core of the optical fiber, through a cladding of the optical fiber, and out of the optical fiber through the lateral side of the optical fiber.

* * * * *